United States Patent [19]

Nohira et al.

[11] Patent Number: 4,845,272

[45] Date of Patent: Jul. 4, 1989

[54] PROCESS FOR THE OPTICAL RESOLUTION OF (±)-CIS OR (±)-TRANS-PERMETHRIC ACID

[75] Inventors: Hiroyuki Nohira, Urawa; Shinichi Yoshida, Misato, both of Japan

[73] Assignee: Kuraray Co., Ltd., Kurashiki, Japan

[21] Appl. No.: 207,229

[22] Filed: Jun. 16, 1988

[30] Foreign Application Priority Data

Jul. 10, 1987 [JP] Japan ................................ 62-173563
Aug. 31, 1987 [JP] Japan ................................ 62-218336

[51] Int. Cl.$^4$ ............................................... C07B 57/00
[52] U.S. Cl. ............................. 562/401; 260/501.16; 562/402; 562/506; 564/304
[58] Field of Search ................... 562/401, 402, 506; 260/501.16; 564/304

[56] References Cited

U.S. PATENT DOCUMENTS

| | | | |
|---|---|---|---|
| 3,842,125 | 10/1974 | Horiuchi et al. | 562/401 |
| 4,289,711 | 9/1981 | Lee | 560/227 X |
| 4,508,919 | 4/1985 | Fogassy et al. | 562/401 |
| 4,542,235 | 9/1985 | Minai et al. | 562/401 |
| 4,599,444 | 7/1986 | Fogassy et al. | 562/401 |

FOREIGN PATENT DOCUMENTS

| | | |
|---|---|---|
| 0010874 | 5/1980 | European Pat. Off. . |
| 0012722 | 6/1980 | European Pat. Off. . |
| 0003060 | 7/1980 | European Pat. Off. . |

OTHER PUBLICATIONS

Patent Abstract of Japan, vol. 5, No. 184(C-80[856], Nov. 21, 1981; & JP-A-56 108 737 (Sumitomo Kagaku Kogyo K.K.) 08-28-81.

*Primary Examiner*—Werren B. Lone
*Assistant Examiner*—Vera C. Clarke
*Attorney, Agent, or Firm*—Oblon, Spivak, McClelland, Maier, & Neustadt

[57] ABSTRACT

A method for optically resolving (±)-cis or (±)-trans-permethric acid which comprises reacting (±)-cis-permethric acid and optically active 1-(p-tolyl)ethylamine or optically active cis-N-benzyl-2-(hydroxymethyl)cyclohexylamine, or reaction (±)-trans-permethric acid and optically active 1-(p-isopropylphenyl)ethylamine, optically active 1-ethylbenzylamine or optically active cis-N-benzyl-2-(hydroxymethyl)cyclohexylamine.

16 Claims, No Drawings

PROCESS FOR THE OPTICAL RESOLUTION OF (±)-CIS OR (±)-TRANS-PERMETHRIC ACID

BACKGROUND OF THE INVENTION

1. Field of the Invention

This invention relate to a process for the optical resolution of (±)-cis or (±)-trans-permethric acid.

2. Description of the Prior Art (±)-Cis or (±)-trans-permethric acid is a carboxylic acid, whose side chain substituent may be modified, and is used; as one ingredient of the esters called pyrethroid. Pyrethroid is an insecticidal component of pyrethrum. The (±)-cis or (±)-trans-permethric acid prepared by chemical synthesis is generally obtained in the form of optically inactive racemates; namely (±)-carboxylic acids. (−)-Cis or (−)-trans-permethric acid contained in the (±)-cis or (±)-trans-permethric acid is far poorer in insecticidal activity than (+)-cis or (+)-trans-permethric acid. Accordingly, there is a demand of the development of a technique in which (±)-cis or (±)-trans-permethric acid is optically resolved in an efficient manner to obtain highly pure (+)-cis or (+)-trans-permethric acid.

Several processes of obtaining an optically active product of cis-permethric acid are known including processes of using, on (±)-cis-permethric acid, resolving agents such as optically active N-benzyl-2-aminobutanol (U.S. Pat. No. 4,599,444), N-(2,2,2-trichloro-1-formamidoethyl)piperazine (U.S. Pat. No. 4,508,919), and 1-phenyl-2-(p-tolyl)ethylamine (U.S. Pat. No. 4,327,038). Also, there are known processes in which the acid is introduced into various derivatives and then resolved. However, the resolving agents used in these processes are relatively expensive and the yield of the optically active cis-permethric acid obtained by the resolution is not high, thus leading to the problem that the optically active cispermethric acid is expensive.

For obtaining an optically active product of transpermethric acid, there have been hitherto proposed a process in which optically active $\beta'$-dimethylamino-$\alpha,\alpha$-dimethyl-$\beta$-phenethyl alcohol is used with (±)-transpermethric acid (Japanese Patent Publication No. 8815/81) and a process in which ephedrine is used with (U.S. Pat. No. 4,328,173). Similar to the optical resolution processes of the cis-permethric acid, these resolving agents are relatively expensive and the optically active transpermethric acid obtained by the resolution is not high in yield. As a result, there arises the same problem that the optically active trans-permethric acid is also expensive.

SUMMARY OF THE INVENTION

It is accordingly an object of the invention to provide a process for optically resolving (±)-cis or (±)-transpermethric acid to obtain intended products of high purity in high yield at low costs.

According to the invention, there is provided a process for the optical resolution of (±)-cis or (±)-transpermethric acid which comprises reacting (±)-cis-permethric acid with a resolving agent of optically active 1-(p-tolyl)ethylamine or optically active cis-N-benzyl-2-(hydroxymethyl)cyclohexylamine, or reacting (±)-transpermethric acid with a resolving agent of optically active 1-(p-isopropylphenyl)ethylamine, 1-ethylbenzylamine or cis-N-benzyl-2-(hydroxymethyl)-cyclohexylamine.

According to the above process, when reacted with an above-defined resolving agent, (+)-permethric acid and (−)permethric acid are, respectively, converted into the corresponding diastereomer salts. These diastereomer salts can be separated from each other by relying on their difference in solubility. More particularly, (±)-cispermethric acid can be optically resolved into (+)-cispermethric acid and (−)-cis-permethric acid. Likewise, (±)-trans-permethric acid can be optically dissolved into (+)-trans-permethric acid and (−)-trans-permethric acid.

DESCRIPTION OF THE PREFERRED EMBODIMENTS

In the practice of the invention, the molar ratio of the resolving agent and the (±)-cis or (±)-trans-permethric acid is not critical and the resolving agent is preferably used in an amount of from 0.5 to 1.2 equivalents, more preferably from 0.8 to 1 equivalent, of the (±)-cis or (±)-trans-permethric acid in order to optically resolve the (±)-cis or (±)-trans-permethric acid efficiently and in high purity. The resolving agent is generally used in a solvent. The solvents used for this purpose include lower alcohols such as methanol, ethanol, 2-propanol, 1-propanol, 1-butanol and the like, lower alkyl methyl ketones such as acetone, methyl ethyl ketone and the like, and water. Of these, methanol is preferred because highly pure, optically active cis or trans-permethric acid can be obtained.

The amount of the solvent, more or less, varies depending upon the type of resolving agent, so that it may be difficult to determine the range of the amount in the same category. Typically, for the optical resolution of (±)-cis-permethric acid, the amount is from 2 to 10 liters per mole of the acid. For the optical resolution of (±)-trans-permethric acid, the amount is from 0.5 to 5 liters per mole of the acid.

The process of the invention is carried out, for example, in the following manner.

(±)-Cis-permethric acid and 0.8 to 1 equivalent, based on the permethric acid, of optically active cis-N-benzyl-2-(hydroxymethyl)cyclohexylamine are added to a solvent, followed by heating for dissolution. Subsequently, the solution is cooled and supersaturated. Preferably, a (±)-cis-permethric acid/(−)-cis-N-benzyl-2-(hydroxymethyl)cyclohexylamine salt or a (−)-cis-permethric acid/(+)-cis-N-benzyl-2-(hydroxymethyl)cyclohexylamine salt is added only in small amounts, thereby permitting the same kind of sparingly soluble diastereomer salt to be precipitated, followed by separation of this salt. The separation of the diastereomer salt may be effected by filtration or centrifugal separation. The thus separated diastereomer salt is treated with a base such as sodium hydroxide, potassium hydroxide, sodium methoxide or the like to collect (−) or (+) cis-N-benzyl-2-(hydroxymethyl)cyclohexylamine, followed by further treatment with an acid such as hydrochloric acid, sulfuric acid, phosphoric acid, p-toluenesulfonic acid or the like to obtain (+)-cis-permethric acid.

For the optical resolution of (±)-cis-permethric acid by the use of 1-(p-tolyl)ethylamine, (+)-cis-permethric acid/(−)-1-(p-tolyl)ethylamine and (−)-cis-permethric acid/(+)-1-(p-tolyl)ethylamine are precipitated as diastereomer salts. These salts are separated and subsequently treated with a base such as sodium hydroxide, potassium hydroxide, sodium methoxide or the like to collect (−) or (+)-1-(p-tolyl)ethylamine, followed by further treatment with an acid such as hydrochloric acid, sulfuric acid, phosphoric acid, p-toluenesulfonic acid or the like to obtain (+) or (−)-cis-permethric acid.

Where (±)-cis-permethric acid is optically resolved by the use of cis-N-benzyl-2-(hydroxymethyl)cyclohexylamine as the resolving agent, (±)-cis-permethric acid and 0.8 to 1 equivalent of optically active cis-N-benzyl-2-(hydroxymethyl)cyclohexylamine based on the (±)-cispermethric acid are added to a solvent and thermally dissolved, followed by cooling for supersaturation. Preferably, a small amount of (+)-trans-permethric acid/(−)-cis-N-benzyl-2-(hydroxymethyl)cyclohexylamine salt or (−)-trans-permethric acid/(+)-cis-N-benzyl-2-(hydroxymethyl)cyclohexylamine salt is added to permit to same kind of sparingly soluble diastereomer salt and separated. The separation of the diastereomer is effected by filtration, centrifugal separation or the like. The resultant diastereomer salt is subsequently treated with a base such as sodium hydroxide, potassium hydroxide, sodium ethoxide or the like to collect (−) or (+)-cis-N-benzyl-2-(hydroxymethyl)cyclohexylamine and further treated with an acid such as hydrochloric acid, sulfuric acid, phosphoric acid, p-toluenesulfonic acid or the like, thereby obtaining (+) or (−)-trans-permethric acid.

For the optical resolution of (±)-cis-permethric acid by the use of optically active 1-(p-isopropylphenyl)ethylamine as an optical resolving agent, (+)-trans-permethric acid/(+)-1-(p-isopropylphenyl)ethylamine salt or (−)-trans-permethric acid/(−)-1-(p-isopropylphenyl)ethylamine salt is precipitated as a sparingly soluble diastereomer salt. This salt is separated, after which it is treated with a base such as sodium hydroxide, potassium hydroxide, sodium methoxide or the like to collect (+) or (−)-1-(p-isopropylphenl)ethylamine, followed by further treatment with an acid such as hydrochloric acid, sulfuric acid, phosphoric acid, p-toluenesulfonic acid or the like, thereby obtaining (+) or (−)-trans-permethric acid.

Moreover, for the optical resolution of (±)-cispermethric acid by the use of optically active 1-ethylbenzylamine as a resolving agent, (+)-trans-permethric acid/(−)-1-ethylbenzylamine salt or (−)-trans-permethric acid/(+)-1-ethylbenzylamine salt is precipitated as a sparingly soluble diastereomer. After separation of the salt, it is treated with a base such as sodium hydroxide, potassium hydroxide, sodium methoxide or the like to collect (−) or (+)-1-ethylbenzylamine, followed by further treatment with an acid such as hydrochloric acid, sulfuric acid, phosphoric acid, p-toluenesulfonic acid or the like to obtain (+) or (−)-trans-permethric acid.

The present invention is described in more detail by way of examples.

EXAMPLE 1

0.42 g (2 mmols) of (±)-cis-permethric acid (hereinafter abbreviated as (±)-1) and 0.27 g (2 mmols) of (−)-1-(p-tolyl)ethylamine (hereinafter abbreviated as (−)-2) were added to 6 ml of methanol and heated for dissolution, followed by gradual cooling to room temperature. The solution was allowed to stand overnight, after which the resultant crystals were filtered to obtain 0.31 g (0.90 mmols) of (+)-1/(−)-2 salt.

This salt was recrystallized from 3.9 ml of methanol to obtain 0.20 g (0.57 mmols) of (+)-1/(−)-2 salt. The yield based on the employed (±)-1 was 57.0%. m.p. = 194°–199° C. and $[\alpha]_{589} = 28.3°$ (C = 1, methanol). 1 ml of a 1N sodium hydroxide aqueous solution was added to the salt and subjected to ether extraction. To the resultant aqueous phase was added 1.1 ml of 1N hydrochloric acid, which was extracted with ether, followed by drying the resultant organic phase with anhydrous sodium sulfate and removing the solvent by distillation under reduced pressure to obtain 0.12 g (0.57 mmols) of (+)-1. The yield was 57.0%. m.p. = 88°–90° C. and $[\alpha]_{589} = +31.6°$ (C = 1, chloroform). The optical purity was 98.1%.

EXAMPLE 2

0.42 g (2 mmols) of (±)-1 and 0.44 g (2 mmols) of (+)-cis-N-benzyl-2-(hydroxymethyl)cyclohexylamine (hereinafter abbreviated as (+)-3) were added to 11 m of methanol and heated for dissolution, followed by gradual cooling to room temperature. The solution was allowed to stand for 4.5 hours and the resultant crystals were filtered to obtain 0.38 g (0.92 mmols) of (−)-1/(+)-3 salt.

The salt was recrystallized from 9 ml of methanol to obtain 0.31 g (0.73 mmols) of (−)-1/(+)-3 salt. The yield was 73.0% based on the employed (+)-1. m.p. = 183°–185° C. and $[\alpha]_{589} = +18.9°$ (C = 0.6, methanol), 1.1 ml of a 1N sodium hydroxide solution was added to the salt, followed by ether extraction, 1.5 ml of 1N hydrochloric acid was added to the resultant aqueous phase and extracted with ether. The organic phase was dried with anhydrous sodium sulfate and subjected to distillation under reduced pressure to remove the solvent, thereby obtaining 0.13 g (0.62 mmols) of (−)-1. Yield = 62.0%. m.p. = 90°–91° C. and $[\alpha]_{589} = -32.2°$ (C = 1, chloroform), The optical purity was 100%.

EXAMPLE 3

4.18 g (20 mmols) of (±)-1 and 4.39 g (20 mmols) of (−)3 were added to 110 ml of methanol and heated for dissolution, followed by gradual cooling to room temperature. The solution was allowed to stand for 4.5 hours and the resultant crystals were filtered to obtain 3.78 g (8.81 mmols) of (+)-1/(+)-3 salt. The yield based on the starting (±)-1 was 88.1%. m.p. = 183°–185° C. and $[\alpha]_{589} = 18.4°$ (C = 0.7, methanol). 4.4 ml of a 3N sodium hydroxide solution was added to the salt and subjected to ether extraction. 3.2 ml of 6N hydrochloric acid was added to the resultant aqueous phase and extracted with ether, followed by drying the organic phase with anhydrous sodium sulfate and removing the solvent by distillation under reduced pressure to obtain 1.83 g (8.75 mmols) of (+)-1. Yield = 87.5%. m.p. = 87.90° C. and $[\alpha]_{589} = +30.1°$ (C = 1.4, chloroform). The optical purity was 93.5%.

EXAMPLE 4

4.18 g (20 mmols) of (±)=1 and 3.50 g (16 mmols) of (+)-3 were added to 90 ml of methanol and heated for dissolution, followed by gradual cooling to room temperature. The solution was allowed to stand for 4.5 hours and the resultant crystals were filtered to obtain 3.64 g (8.50 mmols) of (+)-1/(−)-3 salt. The yield based on the starting (±)-1 was 85.0%. m.p. = 180°–181° C. and $[\alpha]_{589} = ++17.0°$ (C = 0.7, methanol). 4.0 ml of a 3N sodium hydroxide solution was added to the salt and subjected to ether extraction. 2.5 ml of 6N hydrochloric acid was added to the resultant aqueous phase and extracted with ether, followed by drying the organic phase with anhydrous sodium sulfate and removing the solvent by distillation under reduced pressure to obtain 1.77 g (8.46 mmols) of (−)-1. Yield=84.6%. m.p.=85°–88° C. and [α]₅₈₉=−29.3° (C=1.0, chloroform). The optical purity was 93.5%.

Reference 1

4.18 g (20 mmols) of (±)-1 and 4.23 g (20 mmols) of (−)-1-phenyl-2-(p-tolyl)ethylamine (hereinafter abbreviated as (−)-4) were added to 30 ml of methanol and heated for dissolution, followed by cooling to room temperature. The solution was allowed to stand for 4.5 hours and the resultant crystals were filtered to obtain 5.17 g (12.3 mmols) of crude (−)-1/(+)-4 salt.

The salt was recrystallized from 19 ml of methanol to obtain 3.15 g (7.5 mmols) of (−)-1/(+)-4 salt. The yield based on the starting (±)-1 was 75%. [α]₅₈₉=−27.8°. 3 ml of a 3N sodium hydroxide solution was added to the salt and subjected to ether extraction. 1.5 ml of 6N hydrochloric acid was added to the resultant aqueous phase and extracted with ether, after which the organic phase was dried with anhydrous sodium sulfate and the solvent was removed by distillation under reduced pressure to obtain 1.52 g of (−)-1. Yield=73%. [α]₅₈₉=−15.4° (C=1.0, cloroform). The optical purity was found to be 47.7%.

EXAMPLE 5

0.42 g (2 mmols of (±)-trans-permethric acid (hereinafter abbreviated as (±)-11) and 0.33 g (2 mmols) of (+)-1-(p-isopropylphenyl)ethylamine (hereinafter abbreviated as (+)-12) were added to 3 ml of methanol and heated for dissolution, followed by cooling down to room temperature. The solution was allowed to stand overnight and the resultant crystals were filtered to obtain 0.23 g (0.62 mmols) of (+)-11/(+)-12 salt. The yield based on the starting (+)-11 was 62.0%. m.p.=186°–192° C. and [α]₅₈₉=+13.5° (C=1.5, methanol). 0.7 ml of a 1N sodium hydroxide solution was added to the salt and subjected to ether extraction. 0.8 ml of 1N hydrochloric acid was added to the resultant aqueous phase and subjected to extraction with ether, followed by drying the organic phase with anhydrous sodium sulfate and removing the solvent by distillation under reduced pressure to obtain 0.13 g (0.62 mmols) of (+)-11, Yield=62.0%, m.p.=69°–76° C. and [α]₅₈₉=+26.3° (C=1.2, chloroform). The optical purity was 73.7%.

EXAMPLE 6

0.42 g (2 mmols) of (±)-11 and 0.27 g (2 mmols) of (−)-1-ethylbenzylamine (hereinafter abbreviated as (−)-13) were added to 5 ml of methanol and heated for dissolution, followed by gradual cooling to room temperature. The solution was allowed to stand overnight and the resultant crystals were filtered to obtain 0.21 g (0.61 mmols) of (+)-11/(+)-13 salt. The yield based on the starting (+)-11 was 61.0%. m.p.=186°–191° C. and [α]₅₈₉=+16.6° (C=1.1, methanol). 0.7 ml of a 1N sodium hydroxide solution was added to the salt and subjected to ether extraction. 0.8 ml of 1N hydrochloric acid was added to the resultant aqueous phase and subjected to extraction with ether, followed by drying the organic phase with anhydrous sodium sulfate and removing the solvent by distillation under reduced pressure to obtain 0.12 g (0.57 mmols) of (+)-11. Yield=57.0%, m.p.=69°–76° C. and [α]₅₈₉=+27.6° (C=1.2, chloroform). The optical purity was 77.3%.

EXAMPLE 7

160 g (7.65 mmols) of (±)-11 and 1.03 g (7.62 mmols) of (−)-13 were added to 16 ml of methanol, and heated for dissolution, followed by gradual cooling to room temperature. The solution was allowed to stand overnight and the resultant crystals were filtered to obtain 0.86 g (2.5 mmols) of (+)-11/(−)-13 salt. This salt was recrystallized from 5 ml of methanol to obtain 0.70 g (2.03 mmols) of (+)-11/(−)-13 salt. The yield based on the starting (+)11 was 53.1%. m.p.=187°–193° C. and [α]₅₈₉=+18.9° (C=1), methanol). 3 ml of a 1N sodium hydroxide aqueous solution was added to the salt and extracted with ether. 4 ml of 1N hydrochloric acid was added to the resultant aqueous phase and subjected to extraction with ether, followed by drying the organic phase with anhydrous sodium sulfate and removing the solvent by distillation under reduced pressure to obtain 0.41 g (1.96 mmols) of (+)-11. Yield=51.2%, m.p.=67°–70° C., and [α]₅₈₉=+34.1° (C=1.8, chloroform). The optical purity was 95.5%.

EXAMPLE 8

2.09 g (10 mmols) of (+)-11 and 2.19 g (10 mmols) of (−)-3 were added to 10 ml of methanol and heated for dissolution, followed by gradual cooling to room temperature. The solution was allowed to stand overnight and the resultant crystals were filtered to obtain 1.81 g (4.23 mmols) of (+)-11/(−)-3 salt. The salt was recrystallized from 6.5 ml of methanol to obtain 1.20 g (2.80 mmols) of (+)-11/-(−)-3 salt. The yield on the starting (+)-11 was 56.0%. m.p.=160°–162° C. and [α]₅₈₉=+9.94° (C=1.2, methanol). 3.1 ml of a 1N sodium hydroxide solution was added to the salt and subjected to ether extraction. 3.5 ml of 1N hydrochloric acid was added to the resultant aqueous phase and extracted with ether, followed by drying the organic phase with anhydrous sodium sulfate and removing the solvent by distillation under reduced pressure to obtain 0.58 g (2.77 mmols) of (+)-11. Yield=55.4%, m.p.=67°–72° C., and [α]₅₈₉=+34.7° (C=1, chloroform). The optical purity was 97.2%.

EXAMPLE 9

2.09 g (10 mmols) of (±)-11 and 1.75 g (8 mmols) of (−)-3 were added to 8 ml of methanol and heated for dissolution, followed by gradual cooling to room temperature. The solution was allowed to stand overnight and the resultant crystals were filtered to obtain 1.67 g (3.90 mmols) of (+)-11/(−)-3 salt. The salt was recrystallized from 5.5 ml of methanol to obtain 1.15 g (2.68 mmols) of (+)-11/-(−)-3 salt. The yield on the starting (+)-11 was 53.6%. m.p.=155°–160° C. and [α]₅₈₉=+9.19° (C=1.3, methanol). 3.3 ml of a 1N sodium hydroxide solution was added to the salt and subjected to ether extraction. 4 ml of 1N hydrochloric acid was added to the resultant aqueous phase and extracted with ether, followed by drying the organic phase with anhydrous sodium sulfate and removing the solvent by distillation under reduced pressure to obtain 0.53 g (2.53 mmols) of (+)-11. Yield=50.6%, m.p.=68°–71° C., and [α]₅₈₉=+34.8° (C=1.3, chloroform). The optical purity was 97.5°.

Reference 2

2.09 g (10 mmols) of (±)-11 and 1.35 g (10 mmols) of (+)-2 were added to 10 ml of methanol and heated for dissolution, followed by gradual cooling to room temperature. The solution was allowed to stand overnight and the resultant crystals were filtered to obtain 2.05 g of a salt of both compounds. $[\alpha]_{589} = +4.1°$ (C=1, methanol). This salt was recrystallized from 7.6 ml of methanol to obtain 1.09 g of the salt. $[\alpha]_{589} = +4.4°$ (C=1, methanol). 5 ml of a 1N sodium hydroxide solution was added to the salt and subjected to ether extraction. 1.1 ml of 1N hydrochloric acid was added to the resultant aqueous phase and extracted with ether, followed by drying the organic phase with anhydrous sodium sulfate and removing the solvent by distillation under reduced pressure to obtain 0.65 g of (±)-11. $[\alpha]_{589} = -0.39°$ (C=1, chloroform) and optical purity=1.1%.

Reference 3

2.09 g (10 mmols) of (±)-11 and 1.21 g (10 mmols) of (−)-1-phenylethylamine were added to 7.6 ml of methanol and heated for dissolution, followed by gradual cooling to room temperature. The solution was allowed to stand overnight and the resultant crystals were filtered to obtain 1.52 g of a salt of both compounds. $[\alpha]_{589} = -5.23°$ (C=1, methanol). 5 ml of a 1N sodium hydroxide solution was added to the salt and subjected to ether extraction. 1.1 ml of 1N hydrochloric acid was added to the resultant aqueous phase and extracted with ether, followed by drying the organic phase with anhydrous sodium sulfate and removing the solvent by distillation under reduced pressure to obtain 0.96 g of (−)-11. $[\alpha]_{589} = -5.21°$ (C=1, chloroform) and optical purity=14.6%.

Reference 4

2.09 g (10 mmols) of (±)-11 and 1.77 g (10 mmols) of (−)-3-methyl-2-(p-tolyl-butylamine were added to 22 ml of methanol and heated for dissolution, followed by gradual cooling to room temperature. The solution was allowed to stand overnight and the resultant crystals were filtered to obtain 2.51 g of a salt of both compound. $[\alpha]_{589} = -9.82°$ (C=1, methanol). The salt was recrystallized from 22.6 ml of methanol to obtain 0.89 g of the salt. $[\alpha]_{589} = -8.60°$ (C=1, methanol).

5 ml of a 1N sodium hydroxide solution was added to the salt. 1.1 ml of 1N hydrochloric acid was added to the resultant aqueous phase and subjected to ether extraction, after which the organic phase was dried with anhydrous sodium sulfate and the solvent was removed by distillation under reduced pressure to obtain 0.48 g of (±)-11. $[\alpha]_{589} = -0.43°$ (C=1, chloroform) and optical purity=1.1%.

Reference 5

0.55 g (2.63 mmols) of (±)-11 and 0.45 g (2.63 mmols) of (+)-1-(1-naphthyl)ethylamine were added to 5.3 ml of methanol and heated for dissolution, followed by cooling to room temperature and allowing to stand overnight. The resultant crystals were removed by filtration to obtain 0.42 g of a salt of both compounds. The yield based on the total amount of the (±)-trans-permethric acid was 42%.

This salt was decomposed with sodium hydroxide and hydrochloric acid to obtain 0.23 g (1.1 mmols) of (+)-transpermethric acid. $[\alpha]_{589} = +0.42°$ (C=1.7, chloroform) and optical purity=1.2%.

What is claimed is:

1. A process for the optical resolution of (±)-cis-permethric acid, comprising:
   (i) reacting (±)-cis-permethric acid with either optically active 1-(p-tolyl)ethylamine or optically active cis-N-benzyl-2-(hydroxymethyl)cyclohexylamine to obtain the corresponding diastereomeric salts; and
   (ii) separating said diastereomeric salts.

2. The process of claim 1, wherein said diastereomeric salts are separated by fractional crystallization in a solvent.

3. The process of claim 2, wherein said solvent is a member selected from the group consisting of lower alcohols, lower alkyl methyl ketones and water.

4. The process of claim 3, comprising using methanol as said solvent.

5. The process of claim 1, comprising reacting (±)-cis-permethric acid with 0.5 to 1.2 equivalents of either optically active 1-(p-tolyl)ethylamine or optically cis-N-benzyl-2-(hydroxymethyl)cyclohexylamine.

6. A process for the optical resolution of (±)-cis-permethric acid, comprising:
   (i) reacting (±)-cis-permethric acid with either optically active 1-(p-tolyl)ethylamine or optically active cis-N-benzyl-2-(hydroxymethyl)cyclohexylamine to obtain the corresponding diastereomeric salts;
   (ii) separating the diastereomeric salts by fractional crystallization; and
   (iii) obtaining optically resolved (+)-cispermethric acid or (−)-cis-permethric acid.

7. The process of claim 6, wherein a separated diasteromeric salt product is treated first with a base and then with an acid to obtain either (+)-cis-permethric acid or (−)-cis-permethric acid.

8. The process of claim 6, comprising reacting (±)-cis-permethric acid with 0.5 to 1.2 equivalents of either optically active 1-(p-tolyl)ethylamine or optically cis-N-benzyl-2-(hydroxymethyl)cyclohexylamine.

9. A process for the optical resolution of (±)-trans-permethric acid, comprising:
   (i) reacting (±)-trans-permethric acid with either optically active 1-(p-isopropylphenyl)ethylamine, optically active 1-ethylbenzylamine or optically active cis-N-benzyl-2-(hydroxymethyl)cyclohexylamine to obtain the corresponding diastereomeric salts; and
   (ii) separating said diastereomeric salts.

10. The process of claim 9, wherein said diastereomeric salts are separated by fractional crystallization in a solvent.

11. The process of claim 10, wherein said solvent is at least one member selected from the group consisting of lower alcohols, lower alkyl methyl ketones, and water.

12. The process of claim 11, comprising using methanols as said solvent.

13. The process of claim 9, comprising reacting (±)-trans-permethric acid with 0.5 to 1.2 equivalents of either optically active 1-(p-isopropylphenyl)ethylamine, optically active 1-ethylbenzylamine or optically active cis-N-benzyl-2-(hydroxymethyl)cyclohexylamine.

14. A process for the optical resolution of (±)-trans-permethric acid, comprising:
   (i) reacting (±)-trans-permethric acid with either optically active 1-(p-isopropylphenyl)ethylamine, optically active 1-benzylamine or optically active cisN-benzyl-2-(hydroxymethyl)cyclohexylamine to obtain the corresponding diastereomeric salts;
   (ii) separating said diastereomeric salts through fractional crystallization; and
   (iii) obtaining (+)-trans-permethric acid or (−)-trans-permethric acid.

15. The process of claim 14, wherein a separated diastereomeric salt is first treated with base and then with an acid to obtain either (+)-trans-permethric acid or (−)-trans-permethric acid.

16. The process of claim 14, comprising reacting (±)-trans-permethric acid with 0.5 to 1.2 equivalents of either optically active 1-(p-isopropylphenyl)ethylamine, optically active 1-benzylamine or optically active cis-N-benzyl-2-(hydroxymethyl)cyclohexylamine.

* * * * *